United States Patent
Richards-Kortum et al.

(10) Patent No.: US 6,187,289 B1
(45) Date of Patent: Feb. 13, 2001

(54) ACETIC ACID AS A CONTRAST IN REFLECTANCE CONFOCAL IMAGING OF TISSUE

(75) Inventors: Rebecca Richards-Kortum; Rebekah Drezek, both of Austin, TX (US); Colin Smithpeter, Albuquerque, NM (US); Andres F. Zuluaga, Austin, TX (US)

(73) Assignee: Board of Regents, The University of Texas System, Austin, TX (US)

(*) Notice: Under 35 U.S.C. 154(b), the term of this patent shall be extended for 0 days.

(21) Appl. No.: 09/175,234

(22) Filed: Oct. 20, 1998

Related U.S. Application Data

(60) Provisional application No. 60/062,922, filed on Oct. 20, 1997, and provisional application No. 60/076,985, filed on Mar. 5, 1998.

(51) Int. Cl.[7] ............................ A61K 49/00; A01N 37/00
(52) U.S. Cl. .......................... 424/9.8; 424/9.1; 514/557; 600/407; 600/408
(58) Field of Search ................ 424/9.8, 9.1; 600/407, 600/408; 514/557; 128/920, 922

(56) References Cited

U.S. PATENT DOCUMENTS

| | | | |
|---|---|---|---|
| 4,300,570 | * 11/1981 | Stafl | 128/665 |
| 5,116,328 | * 5/1992 | Dyer et al. | 604/289 |
| 5,648,216 | * 7/1997 | Hershfield et al. | 435/6 |
| 5,697,373 | 12/1997 | Richards-Kortum et al. | |
| 5,836,877 | * 11/1998 | Zavislan | 600/407 |
| 5,842,995 | * 12/1998 | Mahadevan-Jansen et al. | 600/473 |

OTHER PUBLICATIONS

Danforth's Obstetrics and Gynecology 7th edition, pp. 918–921, 1994.*

* cited by examiner

Primary Examiner—Diana Dudash
Assistant Examiner—Shahram Sharareh
(74) Attorney, Agent, or Firm—Fulbright & Jaworski, LLP

(57) ABSTRACT

A method for using acetic acid as a contrast agent during reflectance confocal imaging of normal and neoplastic tissue, particularly epithelium. In one aspect, the invention includes a method of using acetic acid as a contrast agent for confocal imaging of cells, including applying acetic acid to the diagnostic tissue sample in sufficient concentration to induce a small scale alteration of the index of refraction of nuclei in the cells; and imaging such cells using a reflectance confocal imaging system.

20 Claims, 3 Drawing Sheets

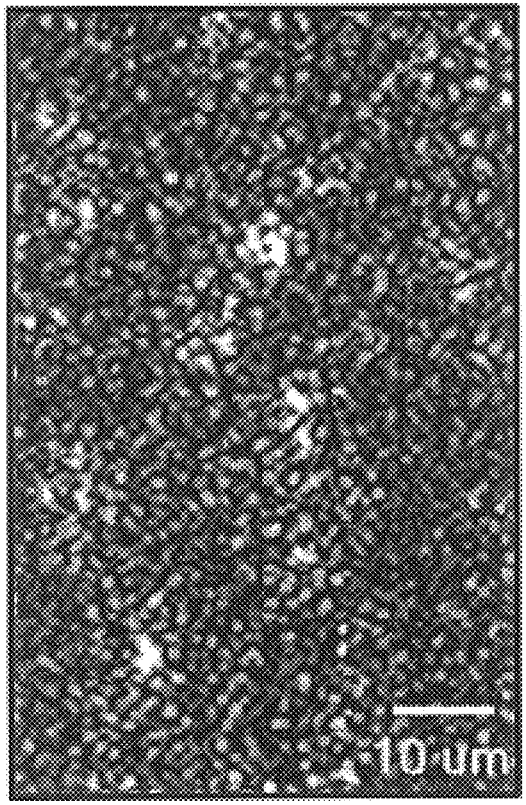 
*FIG. 5A*          *FIG. 5B*

ACETIC ACID AS A CONTRAST IN REFLECTANCE CONFOCAL IMAGING OF TISSUE

CLAIM OF PRIORITY

This application claims priority under 35 USC § 119(e) to U.S. patent application Ser. No. 60/062,922, filed Oct. 20, 1997, and to U.S. patent application Ser. No. 60/076,985, filed Mar. 5, 1998.

TECHNICAL FIELD

The invention relates to methods and apparatus used for optical diagnosis of tissue abnormalities, and more particularly to enhancing detection of tissue abnormalities by reflectance confocal imaging of normal and neoplastic tissue, particularly epithelium.

BACKGROUND

Confocal microscopy is now established as a valuable tool for obtaining high resolution images and 3-D reconstructions of a variety of biological specimens. In particular, confocal microscopy has the capability to quickly provide information about the biochemical and morphological changes that occur as tissue becomes neoplastic.

In reflectance confocal microscopy, a laser light beam is expanded to make optimal use of the optics in the objective. Through an X-Y deflection mechanism, the laser beam is turned into a scanning beam, focused to a small excitation spot by an objective lens onto a specimen. Reflected light is captured by the same objective and, after conversion into a static beam by the X-Y deflection mechanism, is focused onto a photodetector. A confocal aperture (e.g., a pinhole) is placed in front of the photodetector, such that the reflected light from points on the specimen that are not within the focal plane (the so called "out-of-focus" light) where the laser beam was focused will be largely obstructed by the pinhole. In this way, out-of-focus information (both above and below the focal plane) is greatly reduced. This becomes especially important when dealing with thick specimens. The spot that is focused on the center of the pinhole is often referred to as the "confocal spot."

A 2-D image of a small partial volume of the specimen centered around the focal plane (referred to as an optical section) is generated by performing a raster sweep of the specimen at that focal plane. As the laser scans across the specimen, the analog light signal, detected by the photodetector, is converted into a digital signal, contributing to a pixel-based image displayed on a computer monitor attached to the confocal microscope. The relative intensity of the light reflected from the laser "hit" point, corresponds to the intensity of the resulting pixel in the image (typically 8-bit grayscale). The plane of focus (Z-plane) is selected by a computer-controlled fine-stepping motor which moves the microscope stage up and down. Typical focus motors can adjust the focal plane in as little as 0.1 micron increments. A 3-D reconstruction of a specimen can be generated by stacking 2-D optical sections collected in series.

High resolution confocal imaging can be used to obtain near real-time reflected light images of human epithelial tissue in vivo with micron resolution. In vivo confocal imaging can provide information about subcellular morphologic and biochemical changes in epithelial cells which may be useful in the recognition and monitoring of epithelial precancers in organ sites such as the uterine cervix and oral mucosa. Much of the work demonstrating the potential of confocal microscopy to image cell morphology has been carried out in pigmented tissue where melanin within cells provided the confocal signal and image contrast. More recent work has demonstrated confocal microscopy has the ability to visualize structure in amelanotic cells as well. However, the level of native contrast between diagnostically important structures such as the nucleus and the remainder of the cell's contents can vary significantly among cell types due to differences in cell composition.

Indeed, a problem with most optical examination systems and techniques, including reflectance confocal microscopy, is obtaining suitable signals indicative of the property to be measured. Contrast agents have been commonly applied to tissue in vitro and in vivo to enhance the optical return signal of illuminated tissue and thus aid in the extraction of diagnostically useful information from the sample. For example, techniques are commonly used to highlight cellular structures when using light microscopy to examine tissue samples. On a more gross level, sensitive differentiation between normal tissue and neoplasia in various tissue sites has been recently demonstrated through the use of 5-aminolevulinic acid induced protoporphyrin IX fluorescence.

Acetic acid is routinely used during colposcopy, a procedure involving examination of the cervix in situ with a low power microscope, to enhance differences between normal and diseased regions of the cervical epithelium. Areas which may develop into cervical cancer undergo a transient whitening (acetowhitening) visible to the naked eye. While the mechanism behind this phenomenon is not yet fully understood, it is commonly agreed that the higher nuclear density present in abnormal epithelium is a significant factor.

The inventors have determined that it would be desirable to provide a technique for by enhancing the return optical signal for a reflectance confocal microscopy system in a manner that enhances the detection of abnormal tissue. The present invention provides such a technique.

SUMMARY

The invention includes use of acetic acid as a contrast agent during reflectance confocal imaging of normal and neoplastic tissue, particularly epithelium. More particularly, in one aspect, the invention includes a method of using acetic acid as a contrast agent for confocal imaging of cells, including applying acetic acid to the diagnostic tissue sample in sufficient concentration to induce a small scale alteration of the index of refraction of nuclei in the cells; and imaging such cells using a reflectance confocal imaging system.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5(a) and 5(b) showing in vivo confocal image of oral cavity mucosa before (FIG. 5(a)) and after (FIG. 5(b)) addition of acetic acid.

DETAILED DESCRIPTION
Confirmation of Effect

The invention includes use of acetic acid as a contrast agent during reflectance confocal imaging of normal and neoplastic tissue, particularly epithelium. To examine the effects of acetic acid on reflectance at the cellular level, we acquired images of breast cancer cells with a conventional confocal microscope using 800 $\mu$m illumination (e.g., from a Ti:Sapphire laser) and providing 1 $\mu$m spatial resolution. The cells, from the MCF7 early breast cancer cell line, were first imaged in their native state, and then again after the addition of a 6% acetic acid solution. Cell viability was confirmed after exposure to acetic acid through the trypan blue exclusion assay. An example of a suitable confocal microscopy system is set forth in C. Smithpeter, et al., Near real time confocal microscopy of in situ amelanotic cells: sources of signal, contrast agents, and limits of contrast, J. Biomed. Opt., vol. 3, no. 4, pp. 429–436, 1998, which is hereby incorporated by reference.

Figure 1A:
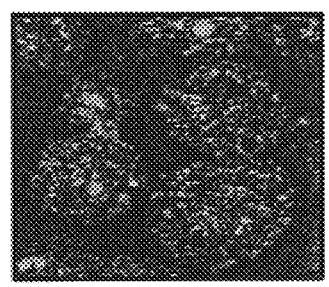
FIGS. 1(a) and 1(b) are scanned photographs of confocal images of MCF7 cells before (left) and after (right) application of acetic acid.
Figure 1B:
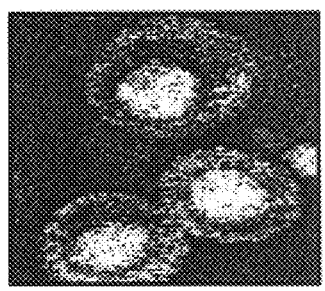

FIGS. 1(a) and 1(b) are scanned photographs of confocal images of MCF7 cells before (left) and after (right) application of acetic acid. In the image of native cells, the nucleus is difficult to resolve. The addition of acetic acid causes a dramatic increase in the signal from the nuclei, resulting in increased signal and image contrast. From these images, it is evident that acetic acid dramatically increases the signal from the nucleus. We have shown that spatial fluctuations in index of refraction provide image contrast in confocal images. In particular, spatial fluctuations which are small compared to the illuminating wavelength provide the greatest increase in signal due to back scattering.

Figure 2A:
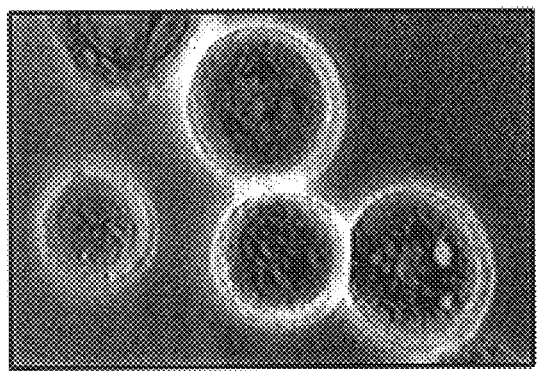
FIGS. 2(a) and 2(b) are scanned photographs of phase contrast images of the same cells before (left) and after (right) application of acetic acid.
Figure 2B:
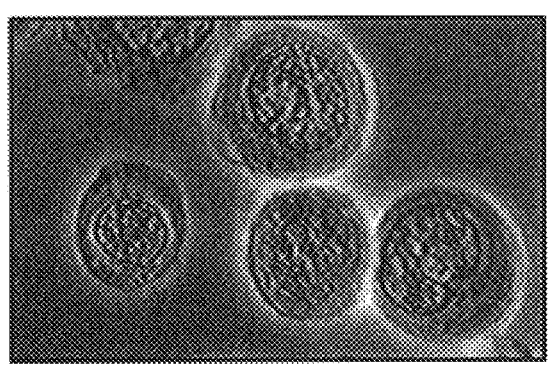

FIGS. 2(a) and 2(b) are scanned photographs of phase contrast images of the same cells before (left) and after (right) application of acetic acid. FIGS. 2(a) and 2(b) demonstrate that acetic acid induces small-scale index variations in the nucleus of a cell, possibly arising from the coagulation of nuclear proteins. These results illustrate that acetic acid can be an important contrast agent for confocal imaging of epithelial cells by highlighting nuclear morphology, which can aid in the discrimination of normal and neoplastic cells.

Figure 3A:
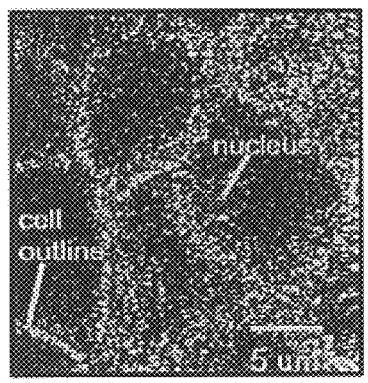
FIGS. 3(a) and 3(b) show reflected light confocal images near the surface of the epithelium (50 μm deep) and near the basement membrane (200 μm deep).
Figure 3B:
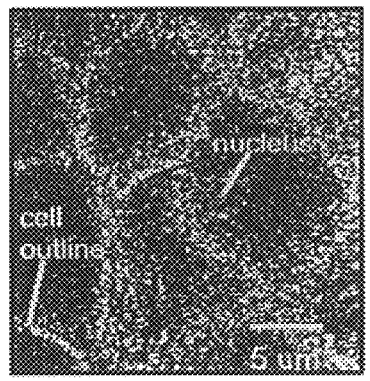

We have also explored the ability of acetic acid as a contrast agent in more complex biological specimens. Images were obtained from cervical biopsies a few minutes after exposure to 6% acetic acid. Biopsies were obtained, snap frozen, stored, and prepared according to protocols described in an earlier paper (A. Mahadevan, et al., Study of the fluorescence properties of normal and neoplastic human cervical tissue, Lasers Surg. Med. 13, 647–655 (1993)). FIGS. 3(a) and 3(b) show reflected light confocal images near the surface of the epithelium (50 $\mu$m deep) and near the basement membrane (200 $\mu$m deep). In both images, the outlines of cells are clearly visible, as well as the cell nuclei. Images obtained before the addition of acetic acid demonstrated similar features; however, signal strength and image contrast were reduced (data not shown).

To demonstrate that confocal imaging using acetic acid to increase the optical return signal could be used to discriminate changes associated with neoplasia, we used the confocal system to obtain images of a colposcopically normal and a colposcopically abnormal biopsy from the same patient before and after the addition of acetic acid. After confocal imaging, transverse frozen sections were cut and stained with hemotoxylin and eosin. Frozen sections were sent to an experienced pathologist for histologic examination. Pathologic diagnoses confirmed clinical impressions at the time of colposcopy.

Figure 4A:
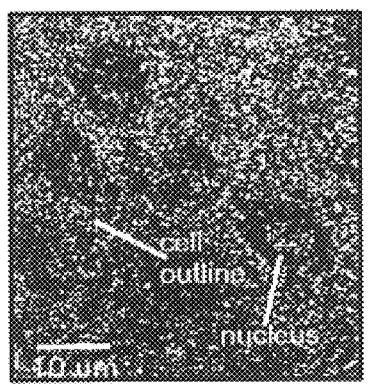
FIG. 4(a) shows an image of a colposcopically normal biopsy, pre-acetic acid.
Figure 4B:
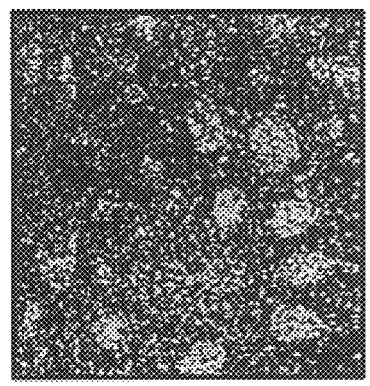
FIG. 4(b) shows an image of a colposcopically normal biopsy, post-acetic acid.
Figure 4C:
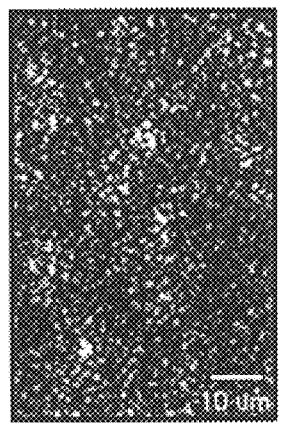
FIG. 4(c) shows an image of a colposcopically abnormal biopsy, pre-acetic acid.
Figure 4D:
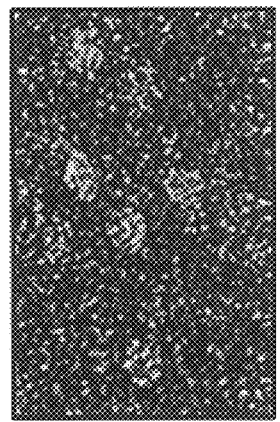
FIG. 4(d) shows an image of a colposcopically abnormal biopsy, post-acetic acid.

Results are shown in FIGS. 4(a)–(d). FIGS. 4(a) and 4(b) show images of the colposcopically normal biopsy, and FIGS. 4(c) and 4(d) contains images of the colposcopically abnormal biopsy which contained a high grade cervical intraepithelial neoplasia. FIGS. 4(a) and 4(c) are pre-acetic acid images of the abnormal biopsy which show the cell outlines and an occasional nucleus. The pre-acetic acid images of the abnormal biopsy show increased reflectivity of both the cell membranes and the nuclei. In addition, the cells are more crowded and irregularly spaced. FIGS. 4(b) and 4(d) are post-acetic acid images which show increased signal from the nuclei in both the normal and abnormal biopsies.

Finally, we have used acetic acid as a contrast agent for in vivo imaging of the oral mucosa of a normal, male volunteer. Visibility of the nuclei was increased after the addition of acetic acid. FIGS. 5(a) and 5(b) showing in vivo confocal image of oral cavity mucosa before (FIG. 5(a)) and after (FIG. 5(b)) addition of 6% acetic acid.

These results show that after the addition of acetic acid, images of tissue can be obtained which illustrate characteristic differences between normal and neoplastic tissue throughout the entire epithelial thickness. Without the application of acetic acid, it is difficult to distinguish the nucleus from the cytoplasm of a cell because of low contrast. Since we have achieved similar results using acetic acid on multiple cell lines (breast and cervical) and tissue types (cervical and oral mucosa) in both in vitro and in vivo situations, acetic acid should be useful for improving nuclear contrast in a variety of organ sites.

Another aspect of the invention is that, unlike most previous work in which images are obtained in real time but then enhanced via time intensive image processing techniques, we present images as they appear at the time of acquisition without any post-processing. These images are representative of what would be possible for clinical applications requiring near video rate imaging and demonstrate the promise of this emerging technology for aiding standard histopathologic diagnosis.

Preferred Method

Having demonstrated that acetic acid can produce measurable differences in optical images of cellular tissue which may be diagnostically useful, the following is the preferred method of embodying this discovery in practice:

(1) Applying acetic acid to the diagnostic tissue sample in sufficient concentration to induce a small scale alteration of the index of refraction of nuclei in the cells. Typical concentrations of acetic acid are 1%–6%, but any medically safe concentration that produces the desired alteration in response is suitable.

(2) Imaging such cells using a reflectance confocal imaging system.

A number of embodiments of the present invention have been described. Nevertheless, it will be understood that various modifications may be made without departing from the spirit and scope of the invention. For example, other apparatus than that described can be used with the inventive method. Accordingly, other embodiments are within the scope of the following claims.

What is claimed is:

1. A method of using acetic acid as a contrast agent for confocal imaging of cells, comprising the steps of:
   (a) applying acetic acid to a diagnostic tissue sample in sufficient concentration to induce an alteration of the index of refraction of nuclei in the cells; and
   (b) imaging the cells using a reflectance confocal imaging system.

2. The method of claim 1, wherein the concentration is about 6%.

3. The method of claim 1, wherein the cells are in vitro.

4. The method of claim 1, wherein the cells are in vivo.

5. The method of claim 1, wherein the cells comprise epithelial cells.

6. The method of claim 1, wherein the cells comprise cervical cells.

7. The method of claim 1, wherein the cells comprise breast cells.

8. The method of claim 1, wherein the imaging generates an image at a time of acquisition, and wherein the method further comprises presenting the image as it appears at the time of acquisition.

9. A method of using acetic acid as a contrast agent for confocal imaging of nuclei of cells, comprising the steps of:
   (a) highlighting nuclear morphology of the cells using acetic acid to induce an alteration of the index of refraction of the nuclei;
   (b) generating an image of the nuclei using a reflectance confocal imaging system; and
   (c) distinguishing the nuclei from cytoplasm of the cells using the image.

10. The method of claim 9, further comprising discriminating changes associated with neoplasia using the image.

11. The method of claim 9, wherein a concentration of the acetic acid is about 6%.

12. The method of claim 9, wherein the cells comprise cervical cells.

13. The method of claim 9, wherein the cells comprise breast cells.

14. The method of claim 9, wherein the image is formed at a time of acquisition, and wherein the method further comprises presenting the image as it appears at the time of acquisition.

15. A method of histopathologic diagnosis using acetic acid as a contrast agent for confocal imaging of nuclei of cells, comprising the steps of:
   (a) highlighting nuclear morphology of the cells using acetic acid to induce an alteration of the index of refraction of the nuclei;
   (b) generating and image of the nuclei using a reflectance confocal imaging system; the image being generated at a time of acquisition;
   (c) presenting the image as it appears at the time of acquisition;
   (d) distinguishing the nuclei from cytoplasm of the cell using the presented image; and
   (e) discriminating changes associated with neoplasia using the presented image.

16. The method of claim 15, wherein a concentration of the acetic acid is about 6%.

17. The method of claim 15, wherein the cells are in vitro.

18. The method of claim 15, wherein the cells are in vivo.

19. The method of claim 15, wherein the cells comprise cervical cells.

20. The method of claim 15, wherein the cells comprise breast cells.

* * * * *